(12) United States Patent
Nakamoto et al.

(10) Patent No.: US 9,044,572 B2
(45) Date of Patent: Jun. 2, 2015

(54) CATHETER HOLDER

(75) Inventors: Ryou Nakamoto, Fujinomiya (JP); Kenta Mitsuhashi, Ashigarakami-gun (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 207 days.

(21) Appl. No.: 13/421,361

(22) Filed: Mar. 15, 2012

(65) Prior Publication Data

US 2012/0172846 A1 Jul. 5, 2012

Related U.S. Application Data

(63) Continuation of application No. PCT/JP2010/065021, filed on Sep. 2, 2010.

(30) Foreign Application Priority Data

Sep. 16, 2009 (JP) .................................. 2009-214998

(51) Int. Cl.
*A61M 25/00* (2006.01)

(52) U.S. Cl.
CPC ............. *A61M 25/002* (2013.01); *Y10S 128/26* (2013.01)

(58) Field of Classification Search
CPC .......... A61M 25/002; A61M 2025/02; A61M 2025/024; A61M 2025/0273; Y10S 128/26
USPC ................. 604/171, 174, 180, 206, 264, 438, 604/533–535
See application file for complete search history.

(56) References Cited

U.S. PATENT DOCUMENTS

| | | | |
|---|---|---|---|
| 6,053,313 A | 4/2000 | Farrell et al. | |
| 2002/0130059 A1 | 9/2002 | Armijo | |
| 2002/0165493 A1* | 11/2002 | Bierman | 604/174 |
| 2006/0047268 A1 | 3/2006 | Stephens | |
| 2007/0043326 A1* | 2/2007 | Navarro et al. | 604/264 |
| 2007/0276333 A1* | 11/2007 | Bierman | 604/180 |

FOREIGN PATENT DOCUMENTS

| | | |
|---|---|---|
| JP | 10-286263 A | 10/1998 |
| JP | 2001-505449 A | 4/2001 |
| JP | 2004-524912 A | 8/2004 |
| JP | 2004-290395 A | 10/2004 |
| JP | 2008-510579 A | 4/2008 |

OTHER PUBLICATIONS

International Search Report (PCT/ISA/210) issued on Nov. 2, 2010, by Japanese Patent Office as the International Searching Authority for International Application No. PCT/JP2010/065021.

* cited by examiner

*Primary Examiner* — Manuel Mendez
(74) *Attorney, Agent, or Firm* — Buchanan Ingersoll & Rooney PC (57) ABSTRACT

A catheter holder which is compact and which can be relatively easily released while holding the unhoused portion of the catheter stably includes: an attachment portion for receiving or being attached to a portion of a holding tube housing a portion of the catheter, and a plurality of hold portions integral with the attachment portion and holding an unhoused portion of the catheter, which is exposed outside the holder tube.

7 Claims, 7 Drawing Sheets

CATHETER HOLDER

This application is a continuation of International Application No. PCT/JP2010/065021 filed on Sep. 2, 2010, and claims priority to Japanese Application No. 2009-214998 filed on Sep. 16, 2009, the entire content of both of which is incorporated herein by reference.

TECHNICAL FIELD

The present invention relates to a catheter holder used for packaging a catheter.

BACKGROUND DISCUSSION

Japanese Unexamined Patent Application Publication No. 2004-290395 describes an example of a catheter that is generally housed in a holder tube wound in a circular manner such that an unhoused portion (a connector and a portion of a sheath) is exposed from the holder tube.

Other ways of packaging involves storing the whole catheter together with the holder tube in a bag by fixing them on a mat board, setting the whole catheter together with the holder tube on a tray and storing the catheter in a bag by fastening one place of the unhoused portion onto the holder tube.

However, a method that involves using a mat board or a tray, because the whole catheter is received on the mat board or in the tray, it is necessary to provide a mat board or a tray conforming in size to the entire catheter. The capacity of the member used for the package is thus relatively large and liable to be bulky as compared with a packaging method involving fastening one place of the unhoused portion onto the holder tube. On the other hand, with the packaging method involving fastening the unhoused portion onto the holder tube, the unhoused portion is held only in one place, so that it is difficult to hold the unhoused portion stably as compared with using a mat board or a tray. In particular, for a highly functionalized catheter, the proximal portion of the catheter is heavy due to the fact that the highly functionalized catheter includes structure such as an electrical connection portion. There thus exists the possibility that the catheter may be relatively easily broken due to the presence of, for example, the structure in which a signal path of an optical fiber or the like passes, and it is difficult to package such a highly functionalized catheter by fastening one place of the unhoused portion onto the holder tube.

SUMMARY

A catheter holder disclosed here is configured to hold a catheter which includes both a housed portion positioned in a holding tube and an unhoused portion positioned outside the holding tube. The catheter holder comprises an attachment portion configured to be attached to a portion of the holding tube housing a portion of the catheter, and a plurality of hold portions integrally formed in one piece as a unitary structure with the attachment portion, with the hold portions configured to hold the unhoused portion of the catheter exposed outside the holding tube. The catheter holder is relatively compact and configured to relatively stably hold the unhoused portion of the catheter.

The attachment portion to be attached to or to fittingly hold a portion of the holder tube does away with structure to accommodate the entire catheter as in a case of previously used mat boards or trays. And the hold portions make it possible to relatively stably hold the unhoused portion of the catheter.

The hold portions can be constructed to include a plurality of sandwiching portions for sandwiching the unhoused portion when closing a first member and a second member which are freely rotatable in a hinged manner. This holding force applied by the sandwiching portions is releasable at one time by opening the first member and the second member so that the catheter can be relatively easily removed.

The catheter holder can also be outfitted with stopper portions provided at the first member and the second member. The stopper portions are engageable with each other for restricting opening of the first member and the second member, and the stopper portions are disengageable from each other for setting a state in which the first member and the second member are relatively openable and closable, thus making it possible to prevent the first member and the second member from being opened unintentionally.

The catheter holder can be further constructed to include engagement portions provided on both the first member and the second member, with the engagement portions being engageable with one another when the first member and the second member are moved to the closed position, and being disengageable with one another when the first member and the second member are moved to the open position.

The hold portions can be configured as concave recesses possessing an undercut shape as seen in cross-section perpendicular to the axis of the concave recess. With this configuration, the holding force of the concave portions can be released at one time by bending the catheter holder and by broadening the plurality of concave portions so that the removal of the catheter is relatively easy.

Another aspect of the disclosure here involves a catheter in combination with a catheter holder, wherein the catheter comprises a housed portion of the catheter positioned in and enclosed by a holding tube, and an unhoused portion positioned outside the holding tube, with the unhoused portion of the catheter comprising a connector connectable to other apparatus and a sheath extending from the connector. The catheter holder comprises: an attachment portion in which is removably positioned a longitudinally extending portion of the holding tube, and a hold portion integrally formed in one piece as a unitary structure with the attachment portion, the hold portion removably holding a part of the unhoused portion of the catheter.

According to another aspect, a catheter holder is configured to hold a catheter which includes both a housed portion positioned in a holding tube and an unhoused portion positioned outside the holding tube. The catheter holder comprises: a frame; a plurality of concave portions integrally formed in one piece as a unitary structure with the frame, with each of the concave portions possessing a size and configuration to receive and removably hold longitudinally spaced apart respective portions of the holding tube; and a plurality of concave recesses integrally formed in one piece as a unitary structure with the frame, with the plurality of concave recesses being spaced apart from the concave portions, and each of the concave recesses possessing a size and configuration to receive and removably hold longitudinally spaced apart respective portions of the housed portion of the catheter.

DETAILED DESCRIPTION

Set forth below with reference to FIGS. 1-5 is a detailed description of one embodiment of a catheter holder disclosed here by way of example. The catheter holder 100 is a holder used for packaging a catheter and generally forms a frame. The catheter holder 100 includes a first component piece 110 (first member) and a second component piece or frame 120 (second member) which are freely rotatable (pivotable) about a hinge. The component pieces 110, 120 are in the form of frames. The catheter holder 100 also includes claws 114, 124 (stopper portions) provided at the component pieces 110, 120 which restrict the component pieces against opening movement. The catheter holder 100 also includes concave portions or grooves 115 (attachment portions) configured to receive or hold (be attached to) a portion of a holding tube 20 that houses the catheter, and a plurality of hold portions 101, 102, 103 configured to receive an unhoused portion 10 of the catheter. All of the hold portions 101, 102, 103 are integrally formed in one piece as a unitary structure with the concave portions or grooves 115. The portion of the catheter housed in and enclosed by the holding tube 20 constitutes a housed portion of the catheter. The unhoused portion 10 of the catheter refers to the portion of the catheter which is exposed outside the holding tube 20 and not housed in or enclosed by the holding tube 20. The unhoused portion 10 of the catheter includes a connector 12 for connecting the catheter with other apparatus, and a sheath 14 extending from the connector 12.

Figure 1:
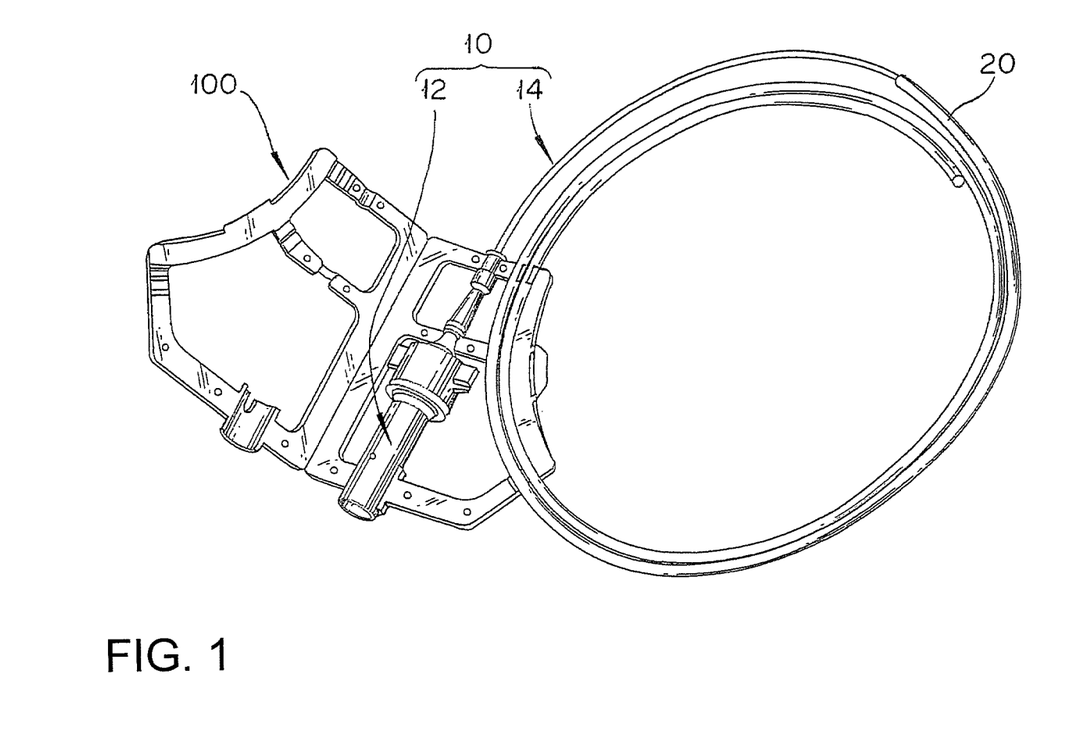
FIG. 1 is a perspective view of a catheter holder, an unhoused portion and a holder tube according to a first embodiment disclosed here by way of example.
Figure 2:
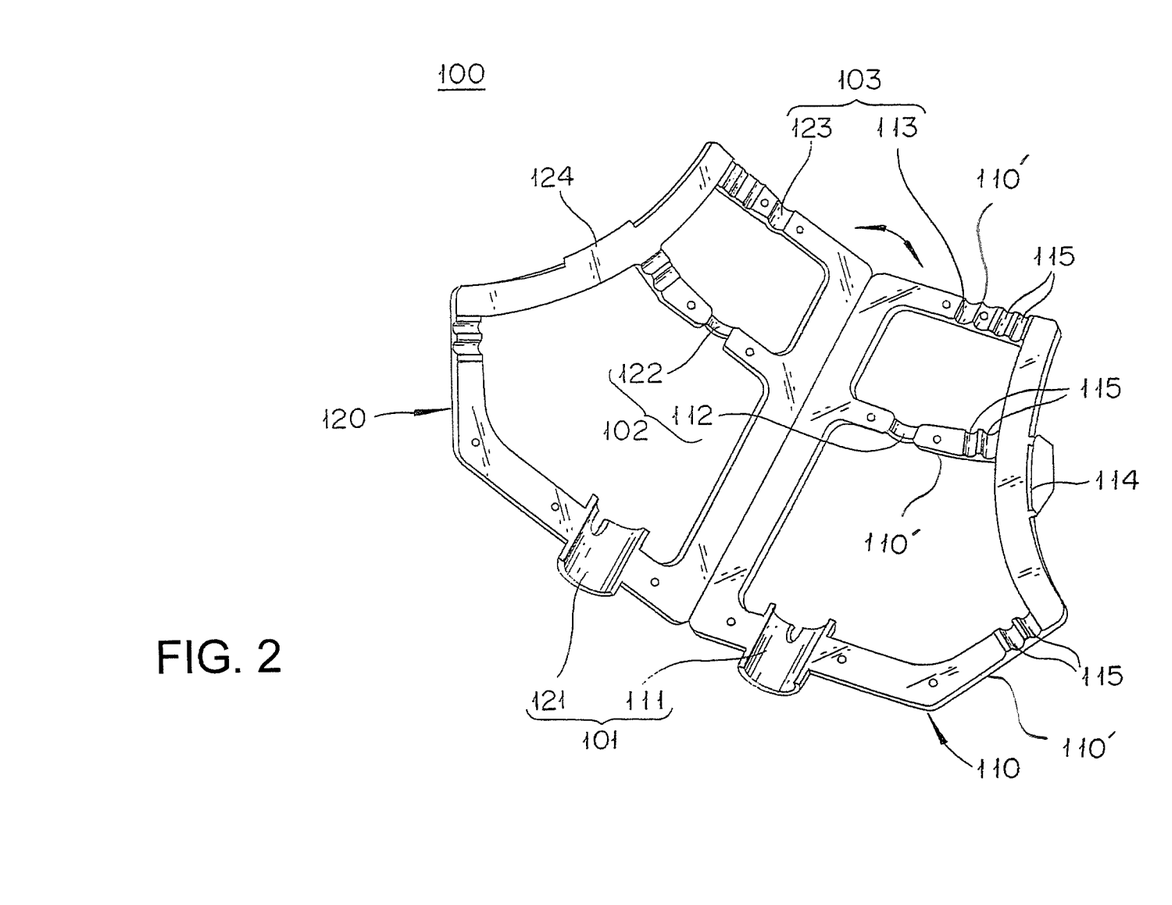
FIG. 2 is a perspective view of the first embodiment of the catheter holder.

With respect to the three hold portions 101, 102, 103 of the catheter holder 100, one hold portion 101 holds the connector 12, and the other two hold portions 102, 103 hold the sheath 14. The hold portions 102, 103 hold the proximal portion of the sheath 14. FIG. 2 shows that the illustrated embodiment of the holder 100 is configured so that the radius of curvature of at least the hold portion 101 is greater than the radius of curvature of the attachment portions 115. FIG. 2 also shows that the illustrated embodiment of the holder 100 is configured so that the radius of curvature of the hold portion 101 is greater than the radius of curvature of the other two hold portions 102, 103.

The plurality of hold portions 101, 102, 103 are a plurality of sandwiching portions for sandwiching the unhoused portion 10 by a mechanism in which the component piece 110 and the component piece 120 are closed. Each of the hold portions 101, 102, 103 is comprised of a concave recess 111, 112, 113 on one of the component pieces 110 and a concave recess 121, 122, 123 on the other component piece 120.

The concave recess 111 and the concave recess 121 have shapes matching the shape of the portion of the connector 12 which is received or held in the concave recesses 111, 112. Similarly, the concave recesses 113, 123, and also the concave recesses 112, 122, possess shapes matching the shapes of the portions of the sheath 14 which the respective concave recesses receive or hold.

Figure 3A:
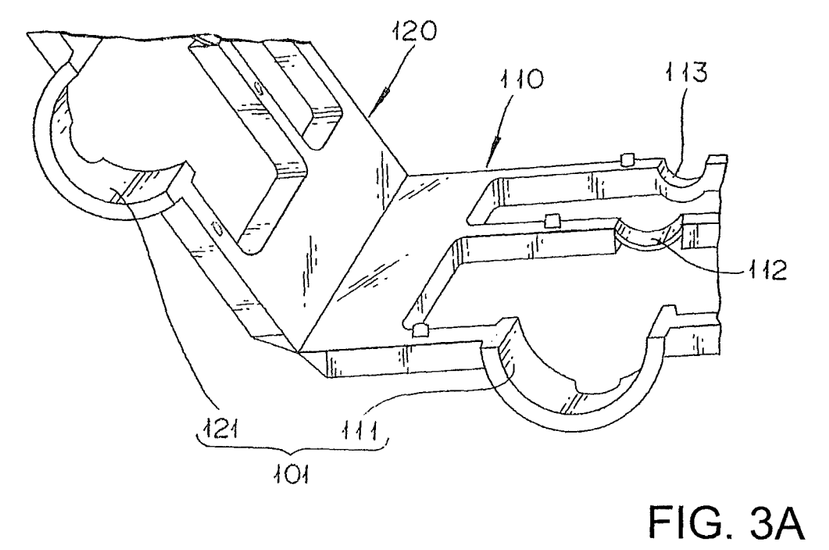
FIG. 3A is a partially enlarged perspective view of the hold portion of the catheter holder according to the first embodiment while the hold portion is being opened.
Figure 3B:
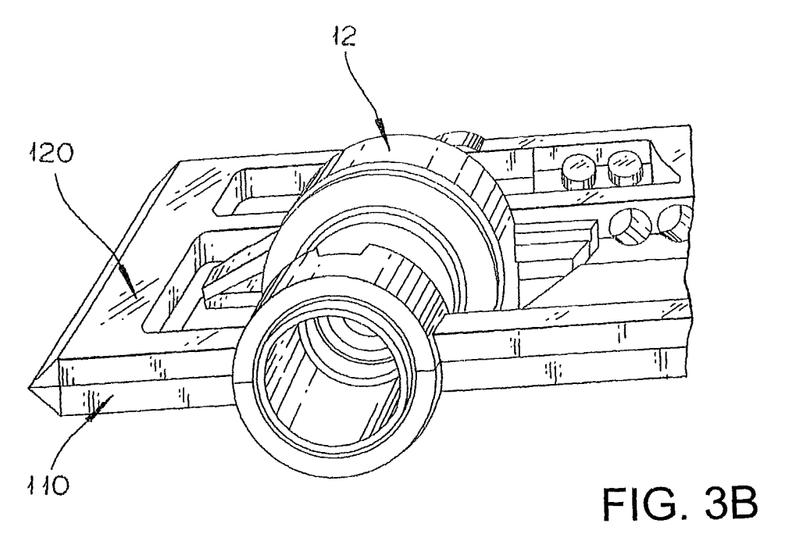
FIG. 3B is a partially enlarged perspective view of a portion of the catheter holder showing the unhoused portion in a state of being housed by closing the hold portion.

A more detailed explanation of the hold portions is given with reference to FIGS. 3a and 3b which shows the concave recess 111 and the concave recess 121 forming the hold portion 101 as an example. The following description also applies to the other two hold portions 102, 103. As shown in FIG. 3B, the region or portion of the connector 12 held or positioned in the concave recess 111 and the concave recess 121 is cylindrical in shape. The concave recess 111 and the concave recess 121 together form a cylindrically shaped through hole in which the connector 12 is positioned. The through hole formed by the concave recesses 111, 112 is sized to receive and hold the connector 12 as shown in FIG. 3B. As mentioned above, the concave portions 113, 123 forming the hold portion 102, and the concave recesses 112, 122 forming the hold portion 103, are similarly configured, though the through hole formed by the concave recesses 113, 123 and the through hole formed by the concave recesses 112, 122 are sized to receive and hold the sheath 14.

The concave recess 111 and the concave recess 121 are each configured to possess a cross-sectional shape, perpendicular to the axial direction of the catheter and the axis of the through hole, that is a semicircular shape. Likewise, the cross-sectional shape of the concave recess 112 and the concave recess 122, perpendicular to the axial direction of the catheter and the axis of the through hole, is a semicircular cross-sectional shape, and the cross-sectional shape of the concave recess 113 and the concave portion 123, perpendicular to the axial direction of the catheter and the axis of the through hole, is a semicircular cross-sectional shape. In other words, the cross-sectional shape of each of the concave recesses 111, 112, 113, 121, 122, 123 is not a undercut shape surrounding the circumference of the catheter axis by an angle greater than 180° and less than 360°. The construction or configuration of the component pieces 110, 120, and thus the hold portions 101, 102, 103, allows the hold portions 101, 102, 103 to lose the holding forces by opening the component pieces 110, 120.

The shape of the connector 12 or the sheath 14 differs depending on the region of the connector/sheath. The connector 12 and the sheath 14 can possess an outer dimension (outer diameter) that varies along the axial direction of the catheter. These portions of different outer dimension (outer diameter) are positioned or held on the catheter holder 100, specifically on the concave recess 111, the concave recess 112 and the concave recess 113, so that even if the component piece 110 and the component piece 120 are opened and the holding force on the connector 12 and the sheath 14 is lost, axial-direction movement of the catheter, and release of the connector 12 and the sheath 14, is inhibited. To further inhibit such deviation of the catheter, it is also possible to provide a protrusion on the outer circumferential surface of the connector 12 and/or of the sheath 14.

Figure 4A:
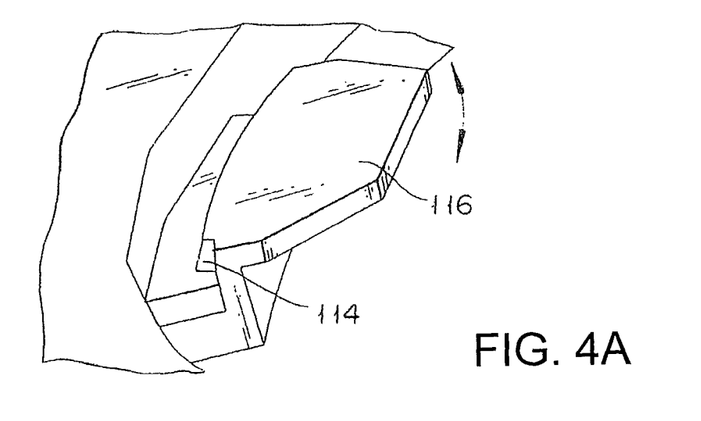
FIG. 4A is a partially enlarged perspective view of a portion of the holder showing an enlarged view of the stopper portion of the first embodiment of the catheter holder.
Figure 4B:
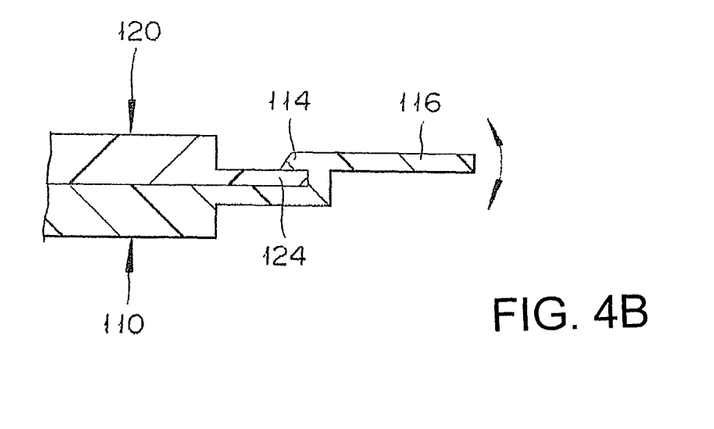
FIG. 4B is a partially enlarged cross-sectional view of the stopper portion of the first embodiment of the catheter holder.

As shown in FIG. 4B, the claws 114, 124 on the component pieces 110, 120 engage each other to restrict the component pieces 110, 120, hold the component pieces 110, 120 in the closed (holding position), and inhibit the component pieces 110, 120 from being opened (inadvertently opened). The claws 114, 124 are nevertheless configured in such a manner that the component pieces 110, 120 are openable and closable. In the illustrated embodiment, the claw 114 of the component piece 110 is integrally provided in one piece with a push portion 116. When the claws 114, 124 are engaged with one another to hold the component pieces 110, 120 in the closed position, the claws 114, 124 can be released from one another to open the component pieces 110, 120 by pressing the push portion 116 to incline the claw 114 and release the hooking engagement between the claw 114 on the component piece 110 and the claw 124 on the other component piece 120.

The illustrated embodiment of the catheter holder 100 includes one set of claws 114, 124, but it is also possible to include plural sets of claws 114, 124. A single set of the claws 114, 124 makes it possible to obtain a state in which the component piece 110 and the component piece 120 are openable and closable to a hooked or latched state in a relatively simple operation as compared to an alternative construction in which plural sets of claws are provided.

Figure 5:
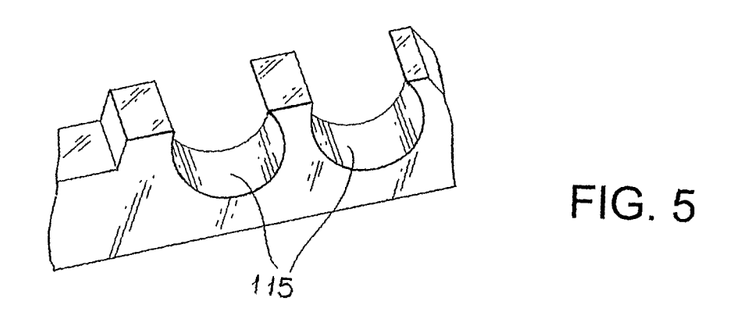
FIG. 5 is a partially enlarged perspective view of the attachment portion of the catheter holder according to the first embodiment.

The concave portions or grooves 115, as shown in FIG. 5, possess a cross-sectional shape, perpendicular to the axial direction of the catheter and the axis of the concave portion, that is not semicircular. Rather, the cross-sectional shape of each of the concave portions 115, perpendicular to the axial direction of the catheter and the axis of the concave portion, is an undercut shape. That is, the wall surrounding each of the concave portions or grooves 115 extends more than 180°, but less than 360°. The wall of the concave portions 115 thus encircles or covers a portion of the outer surface of the holding tube 20 that extends over a circumferential arc of more than 180°, but less than 360°. The concave portions 115 on the two pieces 110, 120 preferably do not possess the same shape. The concave portions 115 on the component piece 110 are configured in the manner shown in FIG. 5, while the component piece 120 includes concave portions, less than a semicircle, which cover the parts of the holder 20 held in the concave portions 115. The holding tube 20 is fitted into and fixed to each of the concave portion 115. Consequently, when opening the component piece 110 and the component piece 120, the holding tube 20 does not inadvertently detach from the catheter holder 100 and remains held in the catheter holder 100. It is possible to fit the holding tube 20 into the concave portion 115 by pushing the holding tube 20 into the concave portion 115 with force or by widening the opening of the concave portion 115 by bending the catheter holder 100.

In the illustrated embodiment shown in FIG. 2, the concave portions or grooves 115 are arranged on a plurality of spaced apart regions of the component piece 110. For example, the illustrated embodiment of the component piece 110 includes a plurality of frame segments 110' (three in the illustrated embodiment), each of which includes concave portions or grooves 115. The illustrated embodiment is configured so that each frame segment 110' includes a plurality of concave portions or grooves 115 arranged side-by-side as shown in FIG. 2.

This first embodiment of the catheter holder achieves various desirable effects. For example, the catheter holder 100 includes the concave portions 115 to which is attached or fixed a portion of the holder tube 20. It is thus not necessary to employ a structure in which the entire catheter is attached as in a case of a mat board or a tray, yet the holder is relatively compact. The presence of the plurality of hold portions 101, 102, 103 also makes it possible to relatively stably hold the unhoused portion 10 of the catheter.

The plurality of hold portions 101, 102, 103 form a plurality of sandwiching portions that sandwich the unhoused portion 10 when the two component pieces 110, 112 are in a closed state. The component pieces 110, 120 are configured so that the hold portions 101, 102, 103 release the holding of the unhoused portion 10 of the catheter at once and at the same time by opening the component pieces 110, 120 (i.e., by moving the component pieces 110, 120 away from one another while pivoting about the hinge), thus facilitating removal of the catheter.

Also, when releasing the fitting between the component piece 110 and the component piece 120 as described above, the holder tube 20 is not fitted on a part of the component piece 120, but rather is always fitted on the component piece 110 at the concave portions 115. That is, when the surgery operator releases the fitting between the component piece 110 and the component piece 120, the surgery operator knows beforehand which one of the component pieces 110, 120 the holder tube 20 is fitted to (i.e., the component piece 110), so that it is possible to carry out the removal of the catheter from the catheter holder efficiently.

If the holder was configured to include a plurality mutually independent hold portions configured to require independent or separate releasings, it would be necessary to hold the connector 12 and/or the sheath 14 every time when releasing each holding, thus repeatedly exerting a load on the catheter. On the other hand, the catheter holder 100 of this embodiment includes plural holdings that are all released at one time and so a load is not repeatedly exerted on the catheter as would otherwise be the case. It is thus possible to suppress the load on the catheter.

The claws 114, 124 engage each other and restrict relative movement of the component piece 110 and the component piece 120 so they remain in the closed state and are not opened. The claws 114, 124 nevertheless are able to be separated or released from one another so that the component piece 110 and the component piece 120 are openable and closable. The claws 114, 124 help prevent the component piece 110 and the component piece 120 from being opened unintentionally.

Figure 6A:
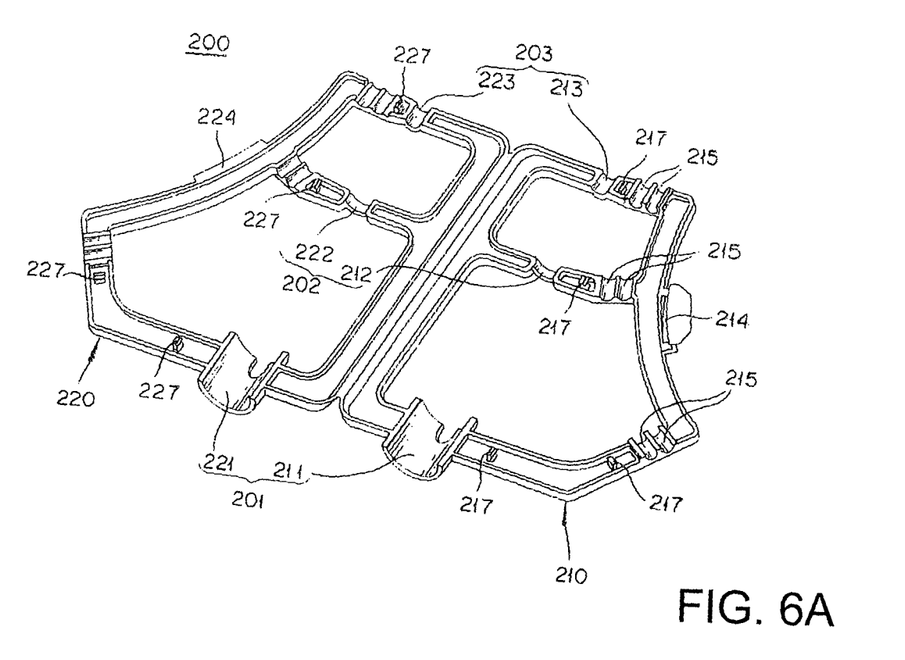
FIG. 6A is a perspective view of a catheter holder according to a second embodiment.
Figure 6B:
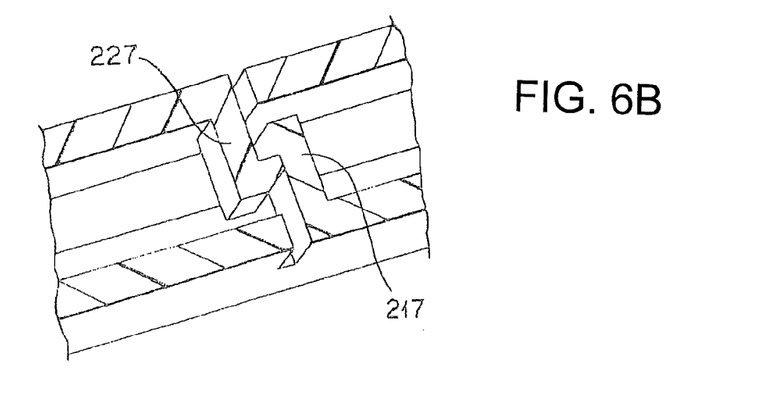
FIG. 6B is a partially enlarged cross-sectional view of the engagement portion of the catheter holder according to the second embodiment disclosed by way of example.

A second embodiment of the catheter holder disclosed by way of example is shown in FIGS. 6A and 6B. This second embodiment is similar to the first embodiment, but differs in that hooks 217, 227 (engagement portion) are included to adjust the holding force for holding the unhoused portion 10. Other features and aspects of the catheter holder which are similar to features described above are identified by common reference numerals, but with the first digit changed from "1" to "2". A detailed description of those common features and aspects of the catheter holder is not repeated.

As shown in FIG. 6A, the hooks 217, 227 are provided at the component piece 210 and the component piece 220 and are engaged with each other by closing the component piece 210 and the component piece 220, and the hooks 217, 227 depart or separate from each other by opening the component piece 210 and the component piece 220.

The inclusion of the hooks 217, 227 makes it possible to adjust the holding force by which the catheter holder 200 holds the unhoused portion 10. The ease with which the component piece 210 and the component piece 220 are opened can also be adjusted adjusting the engagement force between the hooks 217, 227. For example, the holding force can be intensified or increased by intensifying the engagement force between the hook 217 and the hook 227. Conversely, it can be made easier to open the component piece 210 and the component piece 220 by weakening the engagement force between the hook 217 and the hook 227. In other words, the contradictory factors referred to as the holding force and the easiness of opening can be adjusted by changing the engagement force between the hook 217 and the hook 227.

Figure 7A:
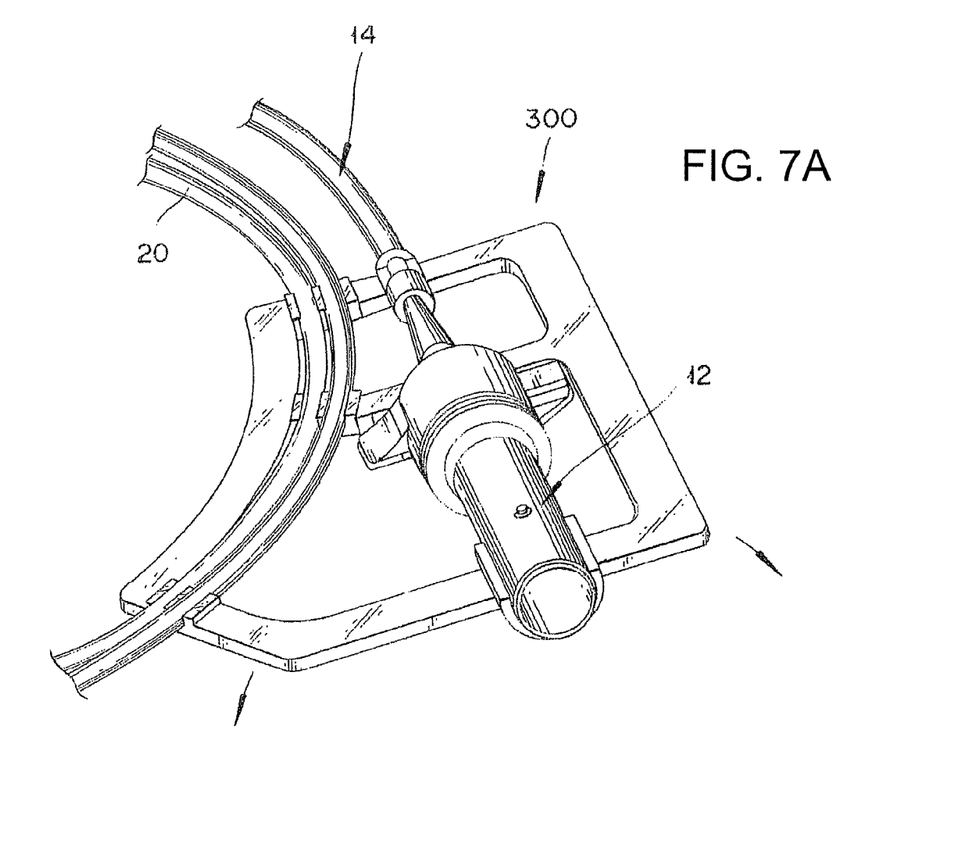
FIG. 7A is a perspective view showing a state of housing an unhoused portion of a catheter holder according to a third embodiment disclosed by way of example.
Figure 7B:
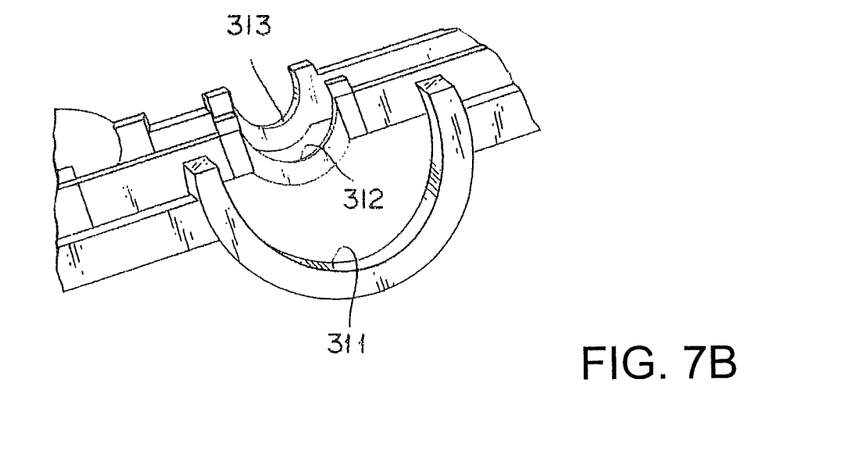
FIG. 7B is a partially enlarged perspective view of the hold portion of the catheter holder according to the third embodiment.

A third embodiment of the catheter holder 300 disclosed by way of example is shown in FIGS. 7A and 7B. This embodiment of the catheter holder 300 includes a component piece approximately similar to the component piece 110 of the first embodiment. But this third embodiment of the catheter holder 300 does not include the second component piece 120 hingedly connected to the one component piece. The third embodiment of the catheter holder 300 thus includes only a single component piece rather than a pair. Additionally, in this third embodiment of the catheter holder 300, the shapes of the plural concave recesses 311, 312, 313 differ from the shapes of the concave recesses 111, 112, 113 of the component piece 110 in the first embodiment.

Each of the concave recesses 311, 312, 313 possesses a cross-sectional shape, perpendicular to the axial direction of the catheter and the axis of the through hole, that does not form a semicircular shape, but instead forms an undercut shape. That is, the wall surrounding each of the concave recesses 311, 312, 313 extends more than 180°, but less than 360°. The wall of the concave recesses 311, 312, 313 thus encircles or covers a portion of the outer surface of the unhoused portion of the catheter extending over a circumferential arc of more than 180°, but less than 360°. In this configuration, the connector 12 and the sheath 14 are fitted into the concave recesses 311, 312, 313 so that the concave recesses 311, 312, 313 firmly hold the connector 12 and the sheath 14.

The catheter holder 300 includes the concave recesses 311, 312, 313 so that by widening the concave recesses 311, 312, 313 through bending of the catheter holder 300, the holding forces applied to the connector 12 and the sheath 14 by the concave recesses 311, 312, 313 are released at once and at the same time, and the removal of the catheter is rather easy. Also, it is possible to adjust the holding force for holding the unhoused portion 10 depending on the depth of the undercut.

The present invention is not limited by the features and aspects associated with the embodiments of the catheter holder described above, and it is possible to apply modifications. For example, the places for holding the unhoused portion are not limited to three places, as it is possible to employ a construction in which the unhoused portion is held at two places or more than three places. Also, a configuration can be employed in which a plurality of hold portions hold only the connector and a configuration can be adopted in which a plurality of hold portions hold only the sheath.

It is also possible to employ an arrangement in which the concave portion of the third embodiment, which is fitted with the unhoused portion, is applied to the first and second embodiments. In other words, it is possible for the hold portion to have a construction including the sandwiching portion and the undercut-shaped concave portion. In this case, even if the first member and the second member (i.e., the two component pieces) are opened, the concave portion holds the unhoused portion, so that when opening the first member and the second member, it is possible to inhibit or prevent the catheter from detaching from the catheter holder unintentionally. Also, when the undercut-shaped concave portion for holding the unhoused portion and the attachment portion are provided on the same side within the first member and the second member, the catheter is not twisted when opening the first member and the second member, which is favorable.

The engagement portion in the embodiment described above is not limited by the hooks as it is also possible, for example, to employ a concave portion and a convex portion which are fitted with each other.

The detailed description above describes features and aspects of embodiments of a catheter holder described as examples of the invention disclosed here. The invention is not limited, however, to the precise embodiments and variations described. Changes, modifications and equivalents can be effected by one skilled in the art without departing from the spirit and scope of the invention as defined in the appended claims. It is expressly intended that all such changes, modifications and equivalents which fall within the scope of the claims are embraced by the claims.

What is claimed is:

1. A catheter holder configured to hold a catheter which includes both a housed portion positioned in a wound holding tube and an unhoused portion positioned outside the wound holding tube, the catheter holder comprising:
a frame;
a plurality of longitudinally spaced apart concave portions integrally formed in one piece as a unitary structure with the frame, each of the concave portions possessing a size and configuration to receive and removably hold longitudinally spaced apart respective portions of the wound holding tube such that portions of the wound holding tube other than the longitudinally spaced apart respective portions are not received and removably held by the plurality of spaced apart concave portions; and
a plurality of longitudinally spaced apart concave recesses integrally formed in one piece as a unitary structure with the frame, the plurality of concave recesses being spaced apart from the concave portions, each of the concave recesses possessing a size and configuration to receive and removably hold longitudinally spaced apart respective portions of the unhoused portion of the catheter such that portions of the unhoused portion other than the longitudinally spaced apart respective portions are not received and removably held by the plurality of spaced apart concave recesses.

2. The catheter holder according to claim 1, wherein the concave portions are undercut so that a wall forming the respective concave portions extends more than 180° but less than 360°.

3. The catheter holder according to claim 2, wherein the concave recesses are undercut so that a wall forming the respective concave recesses extends more than 180° but less than 360°.

4. The catheter holder according to claim 1, wherein the frame comprises a first component piece and a second component piece connected to one another along a hinge allowing the first and second component pieces to be moved toward each other to a closed position, in which the portions of the holding tube and the portions of the unhoused portion are sandwiched between the first and second component pieces, and away from each other to an open position, allowing the portions of the holding tube and the portions of the unhoused portion to be removed from the first and second component pieces.

5. The combination according to claim 4, wherein the concave portions are integrally formed in one piece as a unitary structure with the first component piece, and the second component piece includes additional concave portions integrally formed in one piece as a unitary structure with the second component piece, each of the concave portions of the first component piece being positioned to align with one of the additional concave portions of the second component piece when the first and second component pieces are in the closed position.

6. The combination according to claim 5, wherein the concave recesses are integrally formed in one piece as a unitary structure with the first component piece, and the second component piece includes additional concave recesses integrally formed in one piece as a unitary structure with the second component piece, each of the concave recesses of the first component piece being positioned to align with one of the additional concave recesses of the second component piece when the first and second component pieces are in the closed position.

7. The catheter holder according to claim 1, wherein the frame comprises a first component piece and a second component piece configured to sandwich the portions of the wound holding tube and the portions of the unhoused portion between the first and second component pieces such that the wound holding tube remains at the concave portions on the first component piece while the first component piece is moved away from the second component piece, and the portions of the unhoused portion are removable from the first and second component pieces while the wound holding tube remains at the concave portions on the first component piece.

* * * * *